United States Patent [19]
Chern et al.

[11] Patent Number: 5,750,895
[45] Date of Patent: May 12, 1998

[54] METHOD AND APPARATUS FOR DUAL AMPLITUDE DUAL TIME-OF-FLIGHT ULTRASONIC IMAGING

[75] Inventors: Engmin James Chern, Columbia; David W. Butler, Linthicum, both of Md.

[73] Assignee: The United States of America as represented by the Administrator of the National Aeronautics and Space Administration, Washington, D.C.

[21] Appl. No.: 675,509

[22] Filed: Jul. 3, 1996

Related U.S. Application Data

[63] Continuation-in-part of Ser. No. 501,637, Jul. 12, 1995, abandoned.

[51] Int. Cl.$^6$ ............................................. G01N 29/06
[52] U.S. Cl. ............................................. 73/614; 73/629
[58] Field of Search ........................... 73/602, 610, 612, 73/614, 615, 620, 629, 626; 364/507, 508; 128/660.07, 660.08, 660.09

[56] References Cited

U.S. PATENT DOCUMENTS

| | | | |
|---|---|---|---|
| 4,596,145 | 6/1986 | Smith | 73/626 |
| 4,694,434 | 9/1987 | Von Ramm | 73/626 |
| 4,836,026 | 6/1989 | P'an | 73/620 |
| 4,947,651 | 8/1990 | Moran | 73/602 |
| 5,345,939 | 9/1994 | Engler | 73/602 |

*Primary Examiner*—Christine K. Oda
*Attorney, Agent, or Firm*—Samuel J. Petuchowski; Keith L. Dixon

[57] ABSTRACT

A method and apparatus for ultrasonic imaging which includes scanning a test specimen located in a test fixture in a predetermined scan pattern. Propagating and receiving reflected pulses of ultrasonic energy from an ultrasonic transducer directed to a surface of the test specimen. Detecting and generating data of both the amplitude and the depth of a defect in the test specimen from the pulses received from the test specimen. Merging the data of the amplitude and the data of the depth of the defect into composite data and then displaying the composite data in a three dimensional image whereby a mesh of both amplitude and depth data of the defect is displayed in a single image of the defect.

19 Claims, 6 Drawing Sheets

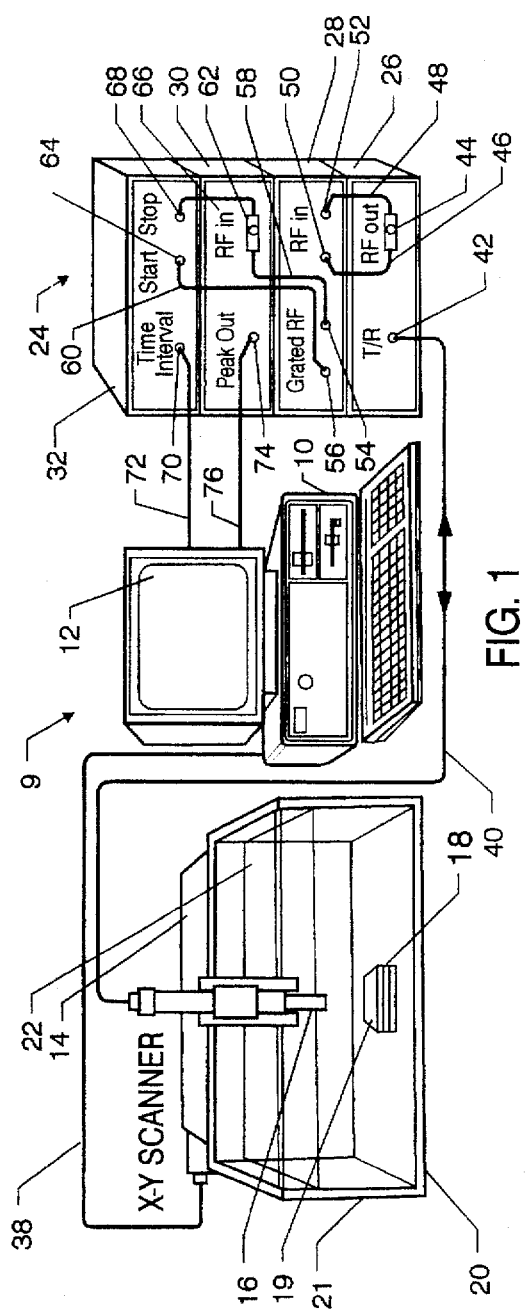
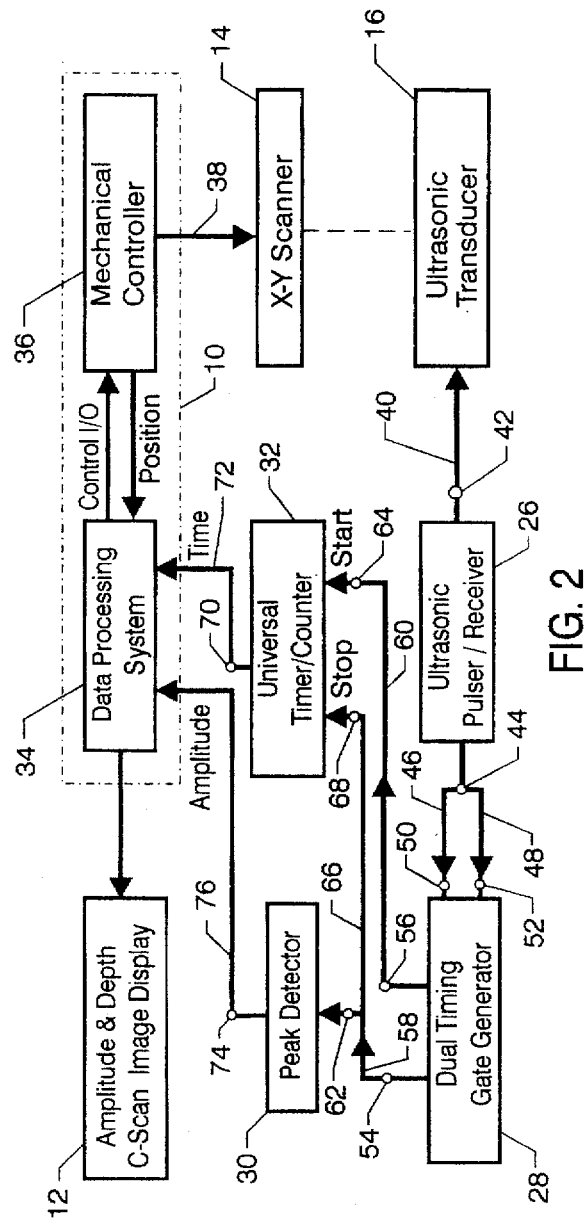

METHOD AND APPARATUS FOR DUAL AMPLITUDE DUAL TIME-OF-FLIGHT ULTRASONIC IMAGING

This application is a Continuation-in-Part of application Ser. No. 08/501,637, filed Jul. 12, 1995, abandoned.

ORIGIN OF THE INVENTION

The invention described herein was made in the performance of work under a NASA contract and by an employee of the United States Government and is subject to Public Law 96-517 (35 U.S.C. § 206 et seq). The contractor has not elected to retain title to the invention.

BACKGROUND OF THE INVENTION

1. Field of the Invention

This invention relates generally to non-destructive testing apparatus and more particularly to an ultrasonic non-destructive testing including a C-scan imaging system.

2. Description of the Prior Art

Conventional state-of-the-art ultrasonic C-scan systems utilized for testing a body of material for internal defects is generally well known. Such systems typically provide a gated peak-detected amplitude imaging capability. Additionally, some of the known prior art systems provide the additional imaging capability of time of flight or depth imaging of the defects. Amplitude imaging provides signal amplitude changes as a function of coordinates, while time of flight imaging provides time interval information of the depth of such defects. Moreover, state-of-the-art ultrasonic C-scan imaging systems acquire either amplitude or time of flight image date for each mechanical scan. Even though two data sets can be acquired and displayed simultaneously, they are displayed separately because there has heretofore been no method or apparatus for merging the two data sets together and therefore correlation is often difficult, cumbersome and human dependent.

SUMMARY

Accordingly, it is an object of the present invention to provide an improvement in the method and apparatus for ultrasonic imaging in non-destructive testing systems.

It is another object of the invention to provide a method and apparatus for providing an improved ultrasonic C-scan imaging system which acquires ultrasonic amplitude data and time of flight data in one data acquisition scan.

It is a further object of this invention to provide a system which not only acquires the ultrasonic amplitude data and time of flight data in one acquisition scan, but also combines the individual amplitude and time of flight C-scan images into one amplitude and depth image display.

It is still another object of the invention to provide a method and apparatus for providing an improved ultrasonic C-scan imaging system which is capable of mapping the specimen geometry and also detecting and characterizing internal defects.

The foregoing and other objects are achieved by both a method and apparatus.

The method includes: locating a test specimen in a test fixture; scanning the test specimen in a predetermined scan pattern, i.e. a rectilinear X and Y axis linear scan pattern over the test specimen; propagating and receiving pulses of ultrasonic energy directed to the test specimen; acquiring both amplitude and time of flight data from the pulses reflected from one or more defects in the test specimen; merging the amplitude and time of flight data into a composite data set; and displaying the composite data set in a three dimensional image whereby a color or grayscale coded mesh of both defect amplitude and depth data of the defect within the body of the test specimen is commonly displayed in a single image of the defects.

The apparatus implementing the method includes: a programmed personal computer which provides control and a monitor therefor; a fluid immersion tank for holding the test specimen; a mechanical scanner assembly located on the tank and having an ultrasonic transducer mounted thereon for transmitting and receiving ultrasonic energy directed to the test specimen; and electronic signal processing circuitry for imaging detected defects on the monitor.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The following detailed description of the invention will be more readily understood when considered together with the accompanying drawings wherein:

FIG. 1 is a perspective view generally illustrative of the major functional components of the subject invention;

FIG. 2 is an electrical block diagram illustrative of the subject invention shown in FIG. 1;

DETAILED DESCRIPTION OF THE INVENTION

Figure 3:
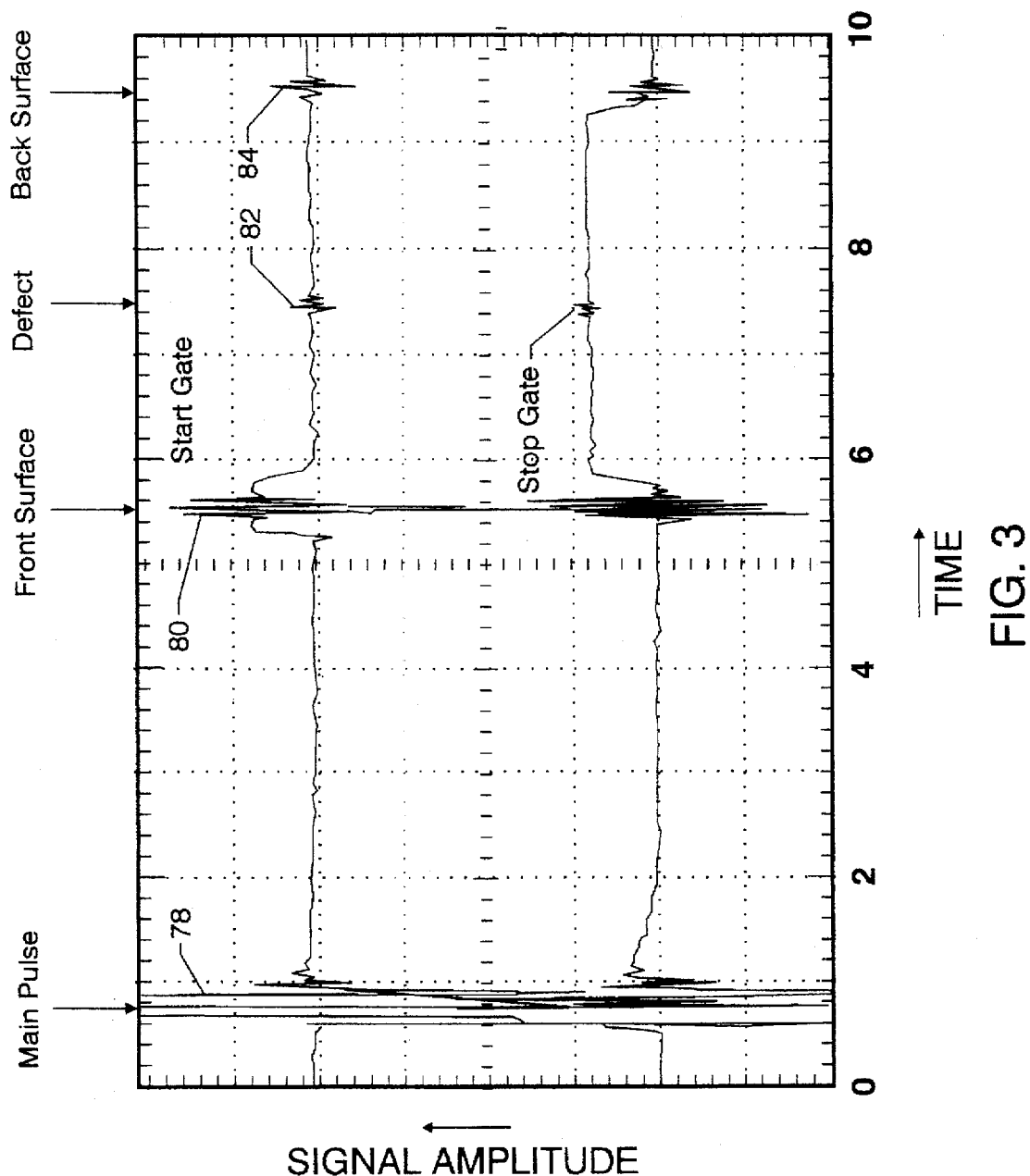
FIG. 3 is a set of time related waveforms helpful in understanding the operation of the subject invention.

Referring now to the drawings and more particularly to FIG. 1, shown thereat are the major functional components of the invention and one which comprises an ultrasonic C-scan system generally designated by reference numeral 9, including a system controller 10 in the form of a personal computer (PC), a video monitor 12 associated with the controller 10, a mechanical scanner assembly 14 which is adapted to hold and move an ultrasonic transducer 16 along two mutually orthogonal X and Y axes over a test specimen 18 which is located in a test fixture 20. The test fixture 20 is shown comprising a tank 21 containing a volume of liquid 22, such as water. The transducer 16 is coupled to electronics system generally designated by reference numeral 24 including a pulser/receiver 26, a dual timing gate signal generator 28, a peak detector 30 and a universal timer/counter 32.

This arrangement, moreover, is shown in block diagrammatic form in FIG. 2; however, the personal computer type controller 10 is shown in FIG. 2 including two sub-systems comprising a data processing system 34 and a mechanical controller 36, the latter being used for controlling the scanner 14. Also, the video monitor 12 is shown as an amplitude and depth C-scan image display.

The ultrasonic transducer 16 is shown in FIG. 2 being mechanically connected to the scanner 14 and typically operates at a frequency between 1 MHz to 30 MHz. The scanner 14 in turn is electrically connected back to the mechanical controller sub-system 36 and the data processing system 34 by means of an electrical cable 38. Further as shown in FIGS. 1 and 2, a cable 40 interconnects the transducer 16 and the pulser/receiver 26 by being coupled to a connector terminal 42. The output of the pulser/receiver 26 is provided at connector terminal 44 to which two cables 46 and 48 connect to RF input terminals 50 and 52 of the dual timing gate generator 28. The gate generator 28 includes two output terminals 54 and 56 to which cables 58 and 60, respectively, connect to an input terminal 62 of the peak detector 30 and a start input terminal 64 of the timer/counter unit 32. Further as shown, a connector cable 66 commonly connects terminals 54 and 62 to the stop input terminal 68 of the timer/counter unit 32. The timer/counter 32 outputs a time interval signal on output terminal 70 which is coupled to the data processing system portion 34 of the PC controller 10 via connecting cable 72. The output of the peak detector unit 30 is coupled from output terminal 74 to the data processing system portion 34 of the PC controller 10 via output terminal 74 and connector cable 76.

Figure 4A:
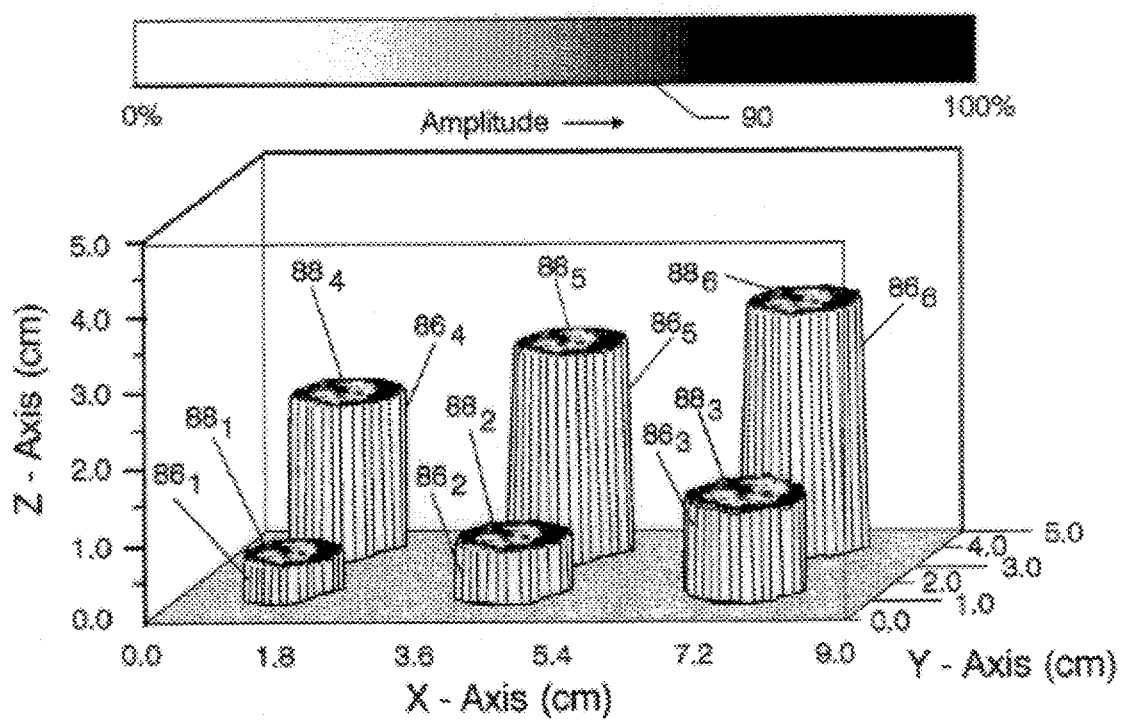
FIGS. 4A and 4B are illustrative of two types of three dimensional graphical displays generated by the subject invention.
Figure 4B:
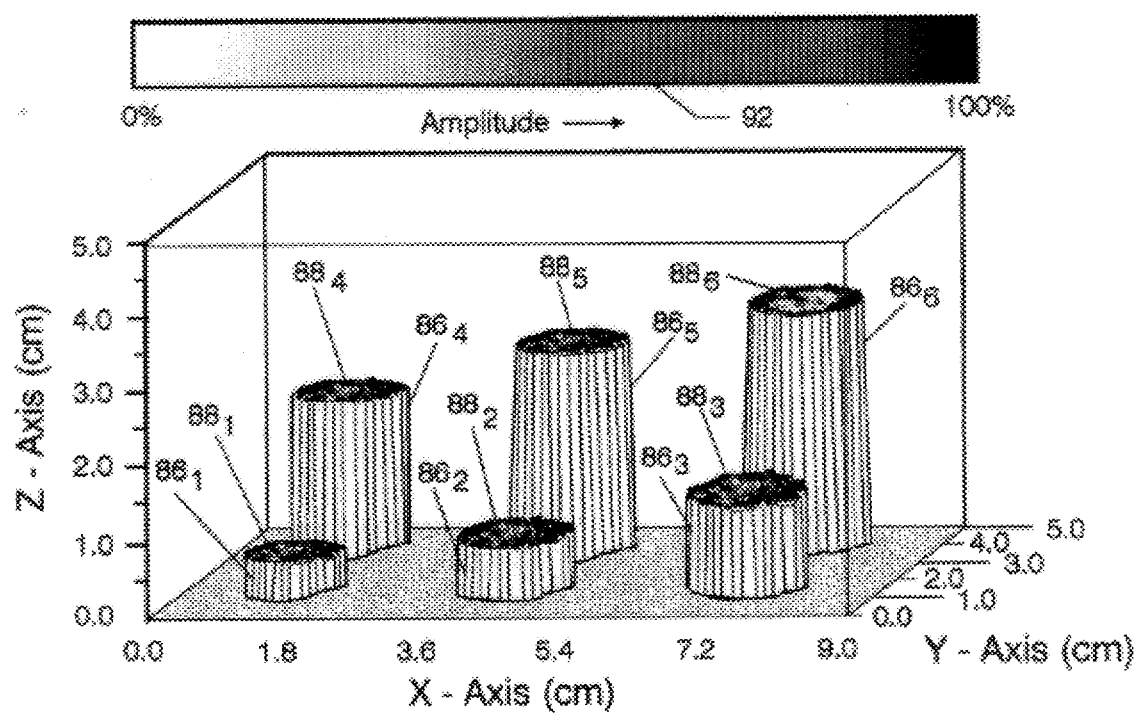

Prior to describing the operation of the ultrasonic non-destructive testing system shown in FIGS. 1 and 2, it should be noted that ultrasonic non-destructive evaluation/testing (NDE) systems is a measuring methodology that is based on elastic-wave propagation principles to evaluate the properties of a specimen. A-scan, B-scan and C-scan are standard ultrasonic NDE terminology. A-scan is simply the imaging of amplitude of ultrasonic pulse returns as a function of time. B-scan refers to the display of a collection of amplitudes along a line such as shown in FIG. 3, whereas C-scan refers to a display of the coordinates of the specimen, for example, scanned along mutually orthogonal X and Y axis coordinates along with the corresponding ultrasonic amplitude of a sensed defect which are displayed along the Z axis. A C-scan is shown in FIGS. 4A and 4B.

Referring again to FIG. 1, in accordance with this invention, an ultrasonic C-scan test procedure is performed with a test specimen, for example specimen 18, being immersed in a tank 21, containing a volume of water 22. The water 22 acts as a coupling agent to enable the propagation of ultrasonic pulses to and from the transducer 16. The scanner 14 is programmed via, the PC controller 10 to scan the specimen 18 in a raster fashion in linear X and Y axis directions. As the transducer 16 scans the specimen 18, ultrasonic pulses such as the main pulse 78 shown in FIG. 3 is directed to the front surface 19 of the specimen 18 where it is reflected as a pulse 80, shown in FIG. 3. Furthermore, ultrasonic energy is reflected from a defect within the body of the specimen 18 as a pulse 82 shown in FIG. 2 and a reflection from the back surface of the specimen 18 is returned to the transducer 16 as pulse 84 shown in FIG. 3.

Referring again to FIGS. 1 and 2, these pulses are coupled to the receiver portion of the pulser/receiver unit 26 which are then respectively coupled to input terminals 50 and 52 of the dual timing gate generator 28 which generates a start gate and a stop gate shown in FIG. 3 which are outputted from terminals 54 and 56 and fed to the input terminals 64 and 68 of the universal timer/counter circuit 32. The delay and width of the two timing gates can be adjusted to accommodate variation in ultrasonic setup and specimen geometry. The depth of the defect is then calculated by the data processing system portion 34 of the PC controller 10 from the time of flight data i.e. the elapsed time between the start gate and stop gate. The depth z is determined using the equation:

$$z = (\Delta t/2) v \quad (1)$$

where $\Delta t$ is the measured round trip or elapsed time and v is the acoustic velocity of the test specimen material. Also, the stop gate information outputted from terminal 56 of the gate generator 28 is internally coupled to the peak detector 30, whose output from terminal 74 is connected to the data processing system portion 34 of the PC control in a connector cable 76.

It is important to note that in this invention, the data processing system portion 34 operates in accordance with stored software programs therein to plot the X and Y axis mechanical scanning positions and associated depth information Z into a pseudo three-dimensional (3-D) display as shown in FIGS. 4A and 4B, along with amplitude information which is indicative of the size of the defect by fusing this information into the Z axis display using either grayscale or color display information to represent amplitude.

Considering now FIGS. 4A and 4B, shown thereat are six defects $86_1$, $86_2$, ... $86_6$ located at six different X and Y axis positions of a display generated on the monitor 12 shown in FIG. 1, with the depth information being displayed along the Z axis. The defects are depicted as generally cylindrical images of varying heights which represent different depths within the specimen 18 of each defect $86_1$ ... $86_6$. Additionally, the amplitude or size of the defect is displayed in the center regions $88_1$, $88_2$, ... $88_6$ of the cylindrical images as a shade of a grayscale 90. This results from the amplitude data derived from the specimen being merged with the depth data acquired. A variation of this is shown in FIG. 4B where the amplitude information in the center regions $88_1$, $88_2$, ... $88_6$ is depicted as color(s) of a plurality of colors representing numerical values in a color scale 92.

Figure 5:
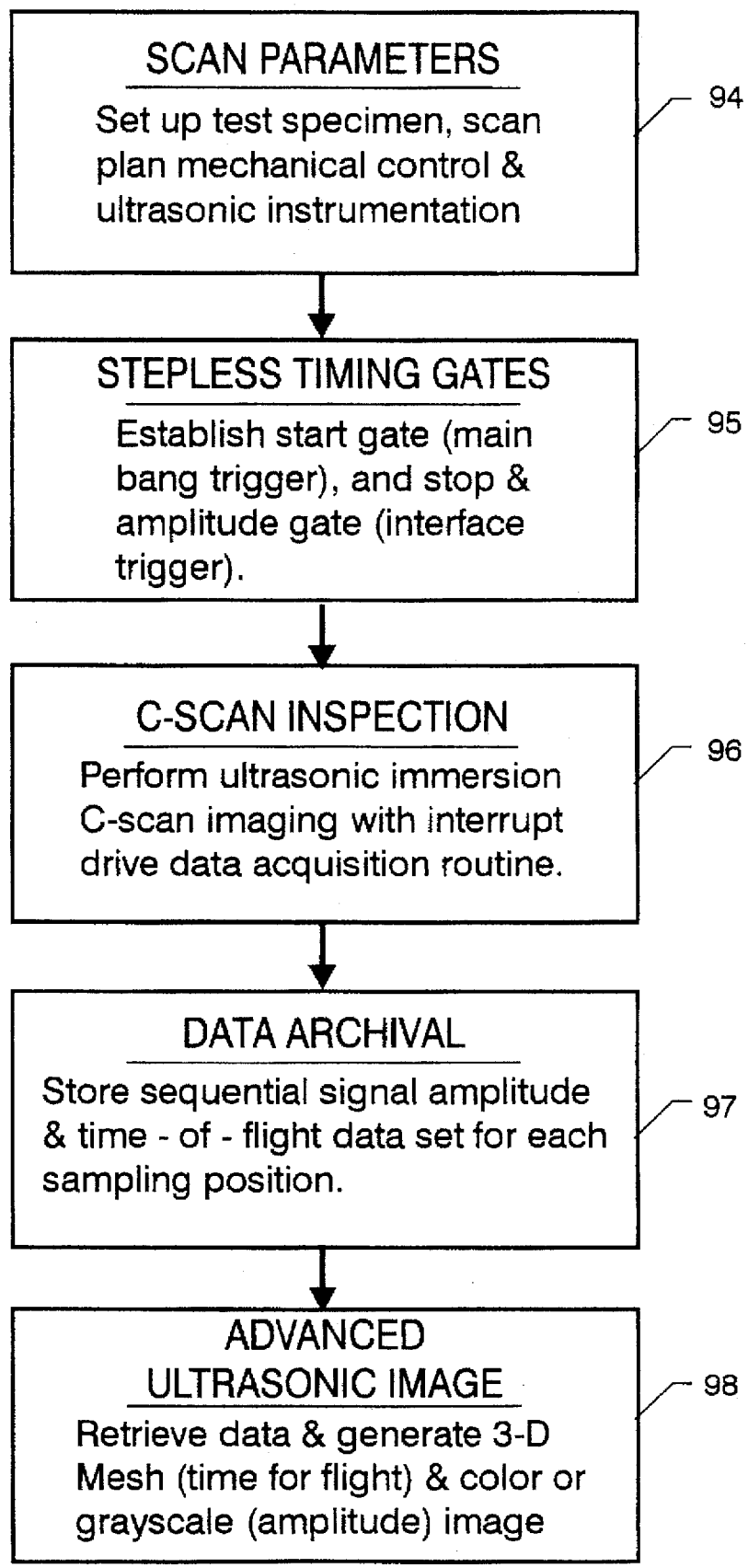
FIG. 5 is a flow chart generally illustrative of the method of the subject invention.

Referring now to FIG. 5, in performing an ultrasonic inspection of a test specimen, one would first set up the test specimen, scan plan, mechanical control and ultrasonic instrumentation as shown by the SCAN PARAMETERS block 94. This is followed by establishing the start gate (main bang trigger) and stop and amplitude gate (interface trigger) as shown by the block 95 entitled STEPLESS TIMING GATES. Next ultrasonic immersion C-scan imaging is performed with an interrupt driven data acquisition routine under computer control as shown by the block 96 entitled C-SCAN INSPECTION. This is followed by sequentially generating and storing a single or dual signal amplitude and time of flight data set for each sampling position over the test specimen as indicated by the block 97 entitled DATA ARCHIVAL. Then the data is retrieved and a 3-D mesh of depth (time of flight) and color or grayscale (amplitude) image is generated as indicated by the block 98 entitled ADVANCED ULTRASONIC IMAGE.

Figure 6:
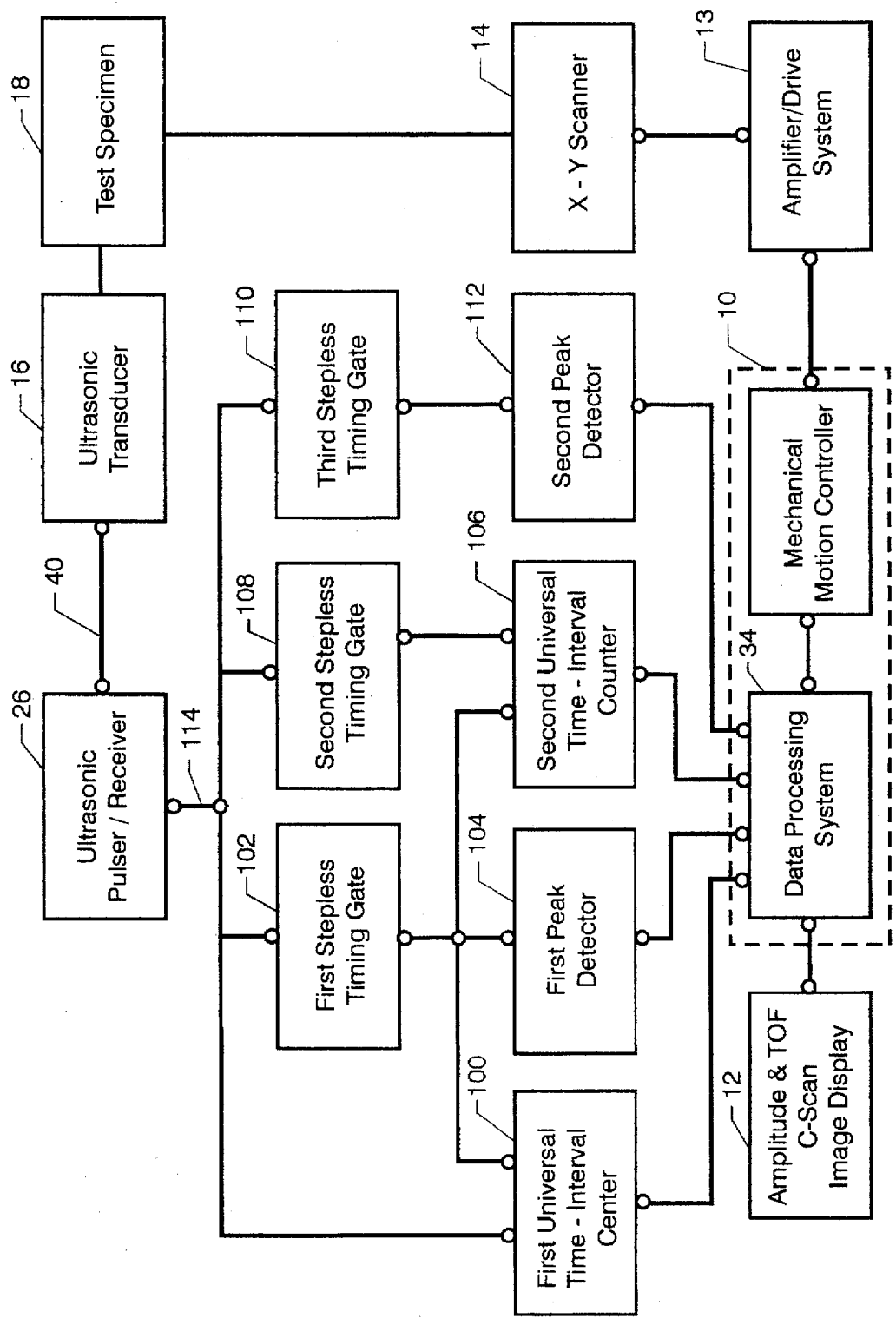
FIG. 6 is an electrical block diagram illustrative of the preferred embodiment of the invention.

Referring now to FIG. 6, an alternative embodiment of the invention is shown in block diagrammatic form. In this embodiment, as in that of FIGS. 1 and 2, system controller 10, comprising data processing system 34 and mechanical controller 36, ultrasonic transducer 16 and ultrasonic pulser/receiver 26 is connected to ultrasonic transducer 16 via cable 40. Pulser/receiver 26 provides electronic pulses (not shown) which are converted by ultrasonic transducer 16 to ultrasonic energy, coupled in turn, to test specimen 18. Pulser/receiver 26 also detects the reflection of ultrasonic energy from the surfaces of specimen 18 and from defects (not shown) within the body of specimen 18 and provides return pulses 80, 82, and 84 (shown in FIG. 3) to stepless timing gates 102, 108, and 110.

A first time-interval counter 100 is started by main pulse 78 (shown in FIG. 3) and stopped by the pulse 80 (shown in FIG. 3) returned by front surface 19 of specimen 18. Thus, the output of first time-interval counter 100 is the round-trip time-of-flight of sound to front surface 19 of specimen 18 and is passed to data processing system 34 to be associated with front surface 19 of specimen 18 at the particular x-y coordinate of the scanning process. A first stepless timing gate 102 is set so that returns after pulse 80 from front surface 19 of specimen 18 are excluded. Pulse 80 returned by front surface 19 is allowed through first stepless timing gate 102 to a first peak detector 104 where it is sampled and an amplitude signal is passed to data processing system 34 to be associated with front surface 19 of specimen 18 at the particular x-y coordinate of the scanning process.

Pulse 80 returned by front surface 19 of specimen 18 and allowed through first stepless timing gate 102 is also used to start a second universal time-interval counter 106. Second universal time-interval counter 106 is stopped, in turn, by return pulse 82 reflected from any defect within specimen 18 and allowed through second stepless timing gate 108 which only passes pulses originating beyond front surface 19 of specimen 18. Similarly, return pulse 84 reflected from the back surface (not shown) of specimen 18 passes through second stepless timing gate 108 and also stops second universal time-interval counter 106 Thus, the output of second time-interval counter 106 is the round-trip time-of-flight of sound to either a defect (not shown) or the back surface (not shown) of specimen 18 and is passed to data processing system 34 to be associated with the particular x-y coordinate of the scanning process.

Third stepless timing gate 110 is set to pass return pulses 82 originating beyond front surface 19 of specimen 18 and prior to return pulse 84 reflected from the back surface (not shown) of specimen 18. A return pulse 82 allowed to pass through third stepless timing gate 110 to a second peak detector 112 where it is sampled and an amplitude signal is passed to data processing system 34 to be associated with a defect (not shown) of specimen 18 at the particular x-y coordinate of the scanning process.

In the case where specimen 18 is irregularly shaped, the alternative dual-amplitude dual-time-of-flight system may be employed, as has been described above with reference to FIG. 6.

Figure 7A:
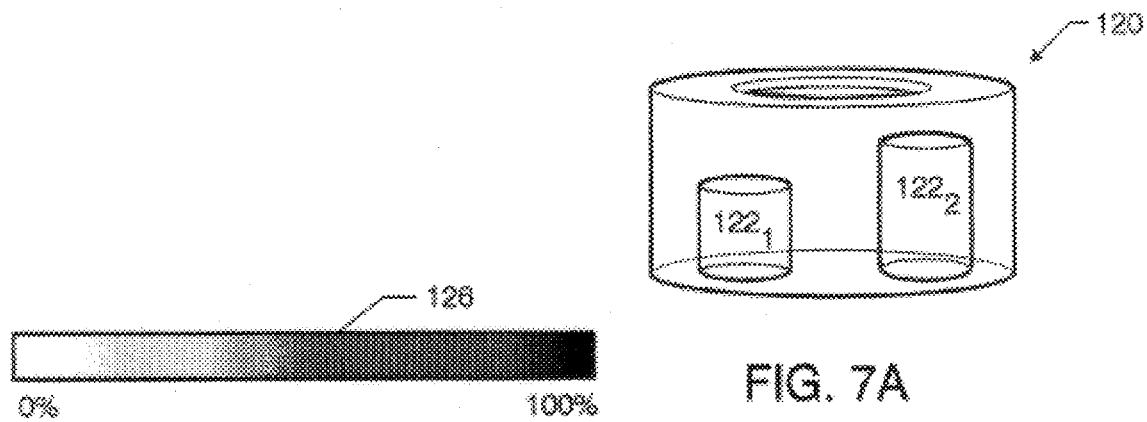
FIG. 7A is a side elevated view of a test specimen.
Figure 7B:
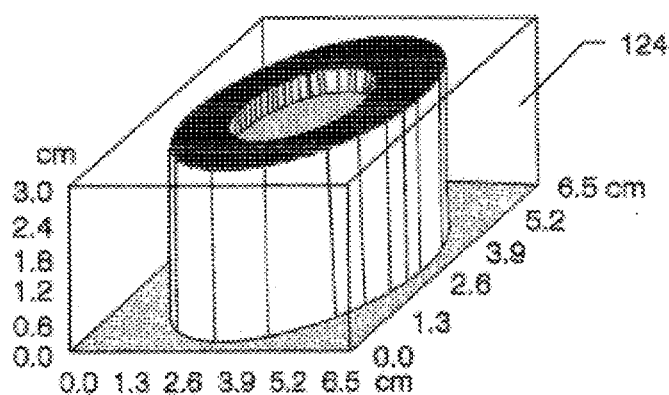
FIGS. 7B and 7C are illustrative of two additional types of three dimensional graphical displays generated by the subject invention.
Figure 7C:
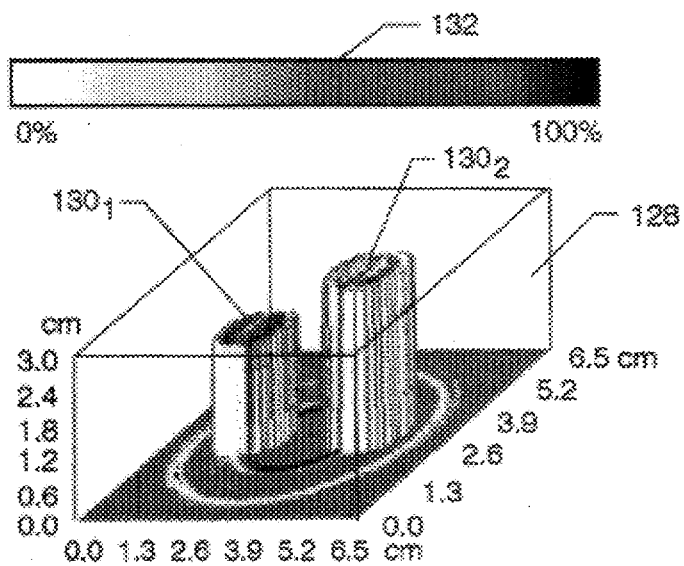

Referring now to FIGS 7A, 7B, and 7C, an irregularly shaped specimen is designated generally by numeral 120 in FIG. 7A. The specific annular shape depicted is shown solely by way of example, but specimen 120 may assume an infinite variety of possible shapes. Cylindrical defects 1221 and 1222 are similarly shown by way of example. In this embodiment, data processing system portion 34 operates in accordance with stored software programs therein, known in the art, to produce the displays shown in FIGS. 7B and 7C. A first pseudo 3-D display designated generally by numeral 124 has X, Y, and Z axes corresponding to the physical axes of specimen 120. Furthermore, first pseudo 3-D display 124 has color or grayscale display information based on color scale 126 representing the shape of specimen 120 as derived by combining time-of-flight and amplitude data provided by first universal time-interval counter 100 and first peak detector 104, both shown in FIG. 6.

A second pseudo 3-D display designated generally by numeral 128 isproduced by data processing system portion 34 (shown in FIG. 6) in accordance with stored software programs therein, by combining time-of-flight and amplitude data provided by second universal time-interval counter 106 and second peak detector 112, both shown in FIG. 6. Second pseudo 3-D display 128 has X, Y, and Z axes corresponding to the physical axes of specimen 120, and color or grayscale display information representing defects 1221 and 1222 in the body of specimen 120. Defects 1221 and 1222 are displayed, respectively, as regions 1301 and 1302, with amplitude represented according to color scale 132.

An advanced digital oscilloscope (not shown) with multi-channel delay trigger and automatic time/amplitude measuring capabilities can, when desirable, be substituted for the dual timing gate 28, universal timer 32, and peak detector 30, all shown in FIG. 2. What is important is the concept of combining two data sets into a common data set for display.

Thus what has been shown and described is a C-scan ultrasonic testing system 9 where depth and amplitude information are merged into a common image which is displayed, for example, on a television type video monitor 12.

Having been shown and described what is considered to be the preferred embodiment of the invention, it should be noted that the same has been made by way of illustration and not limitation. Accordingly, all alterations, modifications and changes coming within the spirit and scope of the invention are herein meant to be included.

We claim:

1. A method of ultrasonic imaging, comprising the steps of:

scanning a test specimen in a predetermined scan pattern;

propagating and receiving reflected pulses of ultrasonic energy directed to a surface of said test specimen;

detecting and generating data of both the amplitude and depth of a defect in said test specimen from the pulses received from said test specimen wherein the step of generating said data includes the step of generating a first timing gate having a start trigger for a timing unit at a front surface of said test specimen and a second timing gate having a stop trigger within a body of said test specimen;

merging said data of said amplitude and said data of said depth of said defect into composite data; and displaying said composite data in three dimensional image whereby a mesh of both amplitude and depth data of said defect is displayed in a single image of said defect.

2. The method of claim 1 wherein the step of scanning comprises scanning the surface of said test specimen in two dimensions.

3. The method of claim 1 wherein said step of scanning comprises linear scanning in mutual orthogonal directions.

4. The method of claim 1 wherein said step of scanning comprises scanning said test specimen in a C-scan mode of operation.

5. The method of claim 4 wherein said step of generating data includes the additional step of acquiring the interval between the moment of emission of said pulses of ultrasonic energy and the return of said pulses from said surface of said test specimen.

6. The method of claim 4 wherein said step of generating data includes the additional step of separately acquiring the amplitude of said pulses from said surface of said test specimen.

7. The method of claim 1 wherein the data of the depth is generated by measuring the time interval between the start trigger and the stop trigger.

8. The method of claim 7 and additionally including the step of determining the depth z of said defect from the expression $z=(\Delta t/2)v$, where $\Delta t$ is the measured time interval between the start trigger and the stop trigger, and v is the acoustic velocity of said material of the test specimen.

9. The method of claim 8 and wherein said step of displaying comprises displaying said composite data as height of said image and said amplitude is displayed as a portion of said image having a grayscale shade signifying a certain value.

10. The method of claim 8 and wherein said step of displaying comprises displaying said composite data as the height of said image and said amplitude is displayed as a portion of said image having a color signifying a certain value.

11. Apparatus for detecting and measuring defects in a test specimen, comprising:

a test fixture for said test specimen;

scanning means located on said test fixture for scanning said test specimen in a predetermined scan pattern;

ultrasonic transducer means located on said scanning means for propagating pulses of ultrasonic energy to and receiving reflected energy from said test specimen;

means for detecting the amplitude of said pulses of ultrasonic energy received back from said test specimen and generating an amplitude signal;

means for determining the depth of a defect in said test specimen from said pulses of ultrasonic energy including means for determining the time interval for an ultrasonic pulse generated by said transducer to travel from an outer surface of said test specimen to said defect and then return to said outer surface and means for generating a start signal when said ultrasonic pulse arrives at said outer surface and a stop signal at the location of said defect, and timer means responsive to said start signal and said stop signal for determining the time difference therebetween, and generating a depth signal;

means for combining said amplitude signal and said depth signal into a composite signal; and means for displaying said composite signal as a meshed image indicative of both amplitude and depth data of said defect in said test specimen.

12. The apparatus of claim 11 wherein said scan pattern comprises a linear scan pattern in two dimensions and said meshed image comprises a three dimensional image.

13. The apparatus of claim 12 wherein said linear scan pattern in two dimensions comprises a linear scan along two mutually orthogonal axes of a rectilinear three axis system.

14. The apparatus of claim 11 wherein said scanning means comprises a portion of an ultrasonic C-scan system.

15. The apparatus of claim 11 wherein said means for determining said time interval includes means for determining the depth z of said defect from the equation $z=(\Delta t/2)v$, where $\Delta t$ is the round trip time of said ultrasonic pulse to travel from said outer surface to said defect and back to said outer surface and v is the acoustic velocity of ultrasonic energy in the constituent material of said test specimen.

16. The apparatus of claim 11, and wherein said means for detecting said amplitude of said pulses include a peak detector for determining said amplitude of said defect.

17. The apparatus of claim 16 and wherein said means for displaying includes means for displaying depth as the height of said meshed image and said amplitude is displayed as a portion of said image having a grayscale shade signifying a certain value.

18. The apparatus of claim 16 and wherein said means for displaying includes means for displaying depth as the height of said meshed image and said amplitude is displayed as a portion of said image having a color of a plurality of colors signifying a certain value.

19. The method of claim 1 wherein the step of detecting and generating data of both the amplitude and depth of a defect in said test specimen includes detecting said reflected pulses received from said test specimen in a time sequence referred to the time of emission of said pulses; and detecting said pulses received from said test specimen in a time sequence referred to the receipt of reflected pulses from said surface of said test specimen.

* * * * *